US009897559B2

(12) United States Patent
He et al.

(10) Patent No.: US 9,897,559 B2
(45) Date of Patent: Feb. 20, 2018

(54) METHOD FOR COLLECTING ACCURATE X-RAY DIFFRACTION DATA WITH A SCANNING TWO-DIMENSIONAL DETECTOR

(71) Applicant: Bruker AXS, Inc., Madison, WI (US)

(72) Inventors: Bob Baoping He, Hercules, CA (US);
Olaf Meding, Karlsruhe (DE);
Christian Maurer, Karlsruhe (DE);
Christoph Ollinger, Karlsruhe (DE)

(*) Notice: Subject to any disclaimer, the term of this patent is extended or adjusted under 35 U.S.C. 154(b) by 142 days.

(21) Appl. No.: 14/979,305

(22) Filed: Dec. 22, 2015

(65) Prior Publication Data

US 2017/0176355 A1 Jun. 22, 2017

(51) Int. Cl.
*G01N 23/20* (2006.01)
*G01N 23/207* (2018.01)

(52) U.S. Cl.
CPC ..... *G01N 23/207* (2013.01); *G01N 23/20016* (2013.01); *G01N 2223/051* (2013.01)

(58) Field of Classification Search
CPC ......... H01J 2237/221; H01J 2237/2809; H01J 37/265; H01J 37/28; G02F 1/0147; G02F 1/155; G02F 2001/1555; G01N 2223/053; G01N 23/20; G01N 2223/0566; G01N 23/207; G01N 23/20008; G01N 23/20016; G01N 2223/076; G01N 23/20025; G01N 23/201; G01N 23/223; G01N 2223/056; G01N 2223/1016; G01N 2223/419; G01N 23/046; G01N 23/203; G01N 23/205; G06T 11/206; G21K 1/06; G06F 19/16; G06F 19/28; G06F 19/703; G06F 9/4446; G06F 3/00; G06F 3/0482; G06F 9/4443; G06K 9/00369; H04N 21/42201; H04N 21/44222; H04N 21/4532; H04N 21/454; H04N 21/252; H04N 21/466; H04N 21/482; H04N 7/163; H04N 2005/91364; H04N 5/782; H04N 2005/91328

USPC .................. 378/70, 71, 79, 81, 86
See application file for complete search history.

(56) References Cited

U.S. PATENT DOCUMENTS 7,035,373 B2 * 4/2006 Omote .................... G21K 1/06
378/71

* cited by examiner

*Primary Examiner* — Irakli Kiknadze
(74) *Attorney, Agent, or Firm* — Benoît & Côté Inc.

(57) ABSTRACT

An X-ray diffraction system uses a two-dimensional detector to detect diffracted X-ray energy at a plurality of radial positions surrounding a sample location, the results at each position being combined to form a final diffraction image. To minimize smearing in the final image, the detector pixel intensities at each position are reapportioned among the pixel locations prior to being combined with the intensities collected at other positions. A two-dimensional pixel array space of the detector is projected onto a cylinder to form a projected pixel array space, and a virtual cylindrical detection surface representative of an ideal cylindrical detector is determined. An overlap between the pixels of the projected pixel array space and the pixels of the virtual cylindrical detection surface is determined, and pixel intensities are reapportioned accordingly. The reapportionment may include dividing each pixel space into subpixels and redistributing the subpixels among adjacent pixels.

19 Claims, 9 Drawing Sheets

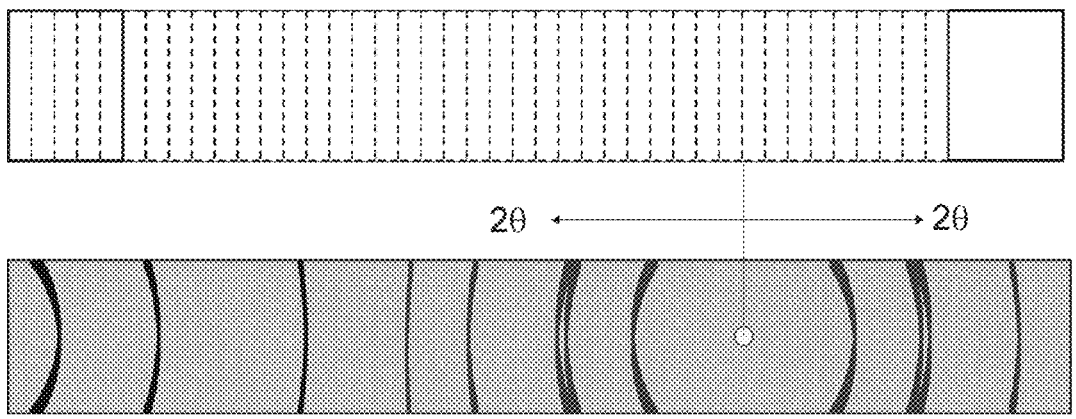
*FIGURE 7*
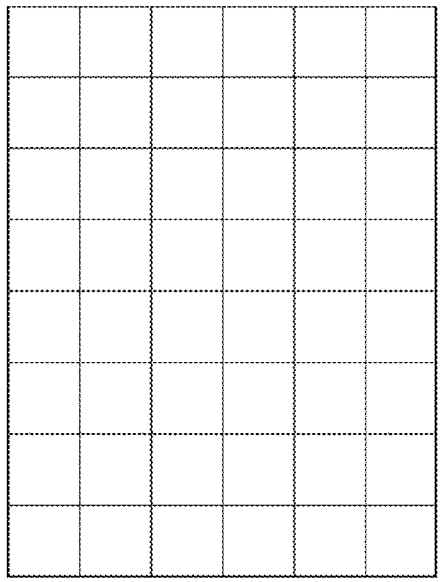 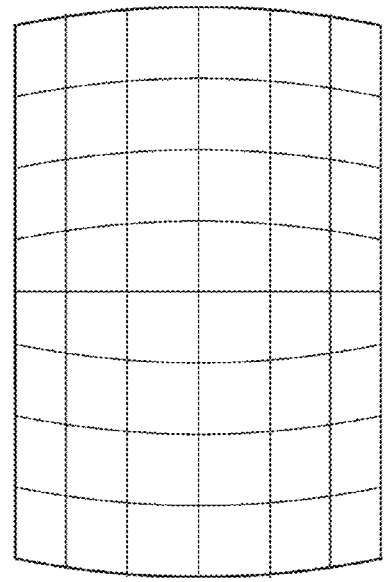
*FIGURE 8A*　　　*FIGURE 8B*

METHOD FOR COLLECTING ACCURATE X-RAY DIFFRACTION DATA WITH A SCANNING TWO-DIMENSIONAL DETECTOR

BACKGROUND OF THE INVENTION

Field of the Invention

This invention relates generally to the field of X-ray diffraction and, more specifically, to the compensation for scattering angle distortions in two-dimensional X-ray detectors.

Description of the Related Art

In the field of x-ray diffraction, radiation with a wavelength, $\lambda$, in the subnanometer range is directed to a crystalline material with a given interatomic spacing, d. When the angle of incidence, $\theta$, relative to the crystalline structure satisfies the Bragg equation, $\lambda=2d \sin \theta$, an interferometrically reinforced signal (the diffracted signal), may be observed leaving the material, with an angle of emission being equal to an angle of incidence, both angles being measured with respect to a direction normal to the interatomic spacing of interest.

Diffracted X-rays from a single crystal sample follow discrete directions each corresponding to a family of diffraction planes, as shown schematically in FIG. 1A. The diffraction pattern from a polycrystalline (powder) sample forms a series diffraction cones, as shown in FIG. 1B, if large numbers of crystals oriented randomly in the space are covered by the incident x-ray beam. Each diffraction cone corresponds to the diffraction from the same family of crystalline planes in all the participating grains. Polycrystalline materials can be single-phase or multi-phase in bulk solid, thin film or fluid. For example, FIG. 2 shows the diffraction pattern of corundum powder collected by a two-dimensional (2D) X-ray detector.

FIG. 3 is a schematic illustration showing the geometry of an X-ray diffraction system in the laboratory coordinates system $X_L Y_L Z_L$. The origin of the coordinate system is the instrument center, or goniometer center. The source X-ray beam propagates along the $X_L$ axis, which is also the rotation axis of the diffraction cones. The apex angles of the diffraction cones are determined by the $2\theta$ values given by the Bragg equation. In particular, the apex angles are twice the $2\theta$ values for forward reflection ($2\theta \leq 90°$) and twice the values of $180°-2\theta$ for backward reflection ($2\theta > 90°$). The $X_L$-$Y_L$ plane is the diffractometer plane. The $\gamma$ angle defines the direction of a diffracted beam relative to the diffraction cone. It is measured within a plane parallel to the $Y_L$-$Z_L$ plane from the point at which the cone intersects the $-z$ portion of the y=0 axis to the point at which the diffracted beam intersects the plane. Thus, a point in the $-Y_L$ portion of the diffractometer plane corresponds to $\gamma=90°$, while a point in the $+Y_L$ portion of the diffractometer plane corresponds to $\gamma=270°$. Thus, the $\gamma$ and $2\theta$ angles form a kind of spherical coordinate system which covers all the directions from the origin, where the sample is located.

An ideal detector to measure a diffraction pattern in three-dimensional (3D) space is a detector with spherical detecting surface, as shown in FIG. 4. The sample is in the center of the sphere, and all of the pixels of the detector are equally distanced from the sample. This configuration, however, is very impractical and, in practice, the detection surface will be flat, cylindrical or with another curved shape. Therefore, the pixel-to-sample distance varies within a detector. Correspondingly, angular coverage of a pixel in the same detector is different depending on the location of the pixel within the detector.

SUMMARY OF THE INVENTION

In accordance with the present invention, a method and apparatus for performing an X-ray diffraction analysis of a sample is provided which avoids scattering angle distortion in the collected data. The sample is first located in a goniometer at the origin of a three-dimensional coordinate system having mutually perpendicular $X_L$, $Y_L$ and $Z_L$ axes. The sample is illuminated with an X-ray beam directed along the $X_L$ axis such that diffracted X-rays from the sample are emitted along a range of diffraction angles. The diffracted X-rays are detected with a two-dimensional X-ray detector having a minimum distance D from a center of the sample along a radial direction in the $X_L$-$Y_L$ plane that is substantially perpendicular to a surface of the detector. The detector surface is planar and has an array of detector pixels located in a two-dimensional pixel array space surrounding the origin. During the diffraction analysis, the detector moves along a circular path relative to the sample at a constant distance therefrom. The movement may be continuous or in a step-wise fashion.

Because the two-dimensional detector shape of the detector array will result in varying images of the diffracted X-rays from one detector position to another, the image at each position is adjusted to reapportion the X-ray intensities detected by each detector pixel. To do this, the two-dimensional pixel array space is projected along the range of diffraction angles onto a cylinder having a radius relative to the $Z_L$ axis of length equal to the distance D to form a projected pixel array space. A virtual cylindrical detection surface on said cylinder is determined which has an array of virtual pixels each of which, in an exemplary embodiment, corresponds to one of the detector pixels. A spatial overlap between pixels of the projected pixel array and the virtual detection surface is then determined, and detected X-ray intensities are then reapportioned among the pixels of the detector based on the overlap such that the reapportioned pixel intensity values represent those which would have been detected by a cylindrical detector having a detection surface at said virtual cylindrical detection surface. In an exemplary embodiment, there is a one-to-one correspondence between the pixels of the projected pixel array space and the virtual pixels of the virtual cylindrical detection surface, although other relative numbers of pixels can also be accommodated.

During the scan, as the detector moves about the sample, it is progressively positioned along a series of different radial directions in the $X_L$-$Y_L$ plane so as to collect diffraction data along a desired angular range, and the pixel intensities are reapportioned at each detector position. The reapportioned pixel intensities collected at each radial position are then combined relative to the diffraction angle so as to generate the overall detection image. The movement of the detector is typically such that diffracted X-rays emitted along the same diffraction angle are detected by the detector for at least two of said plurality of radial directions. Although the diffracted X-rays along each diffraction angle are collected by different pixels at different radial positions of the detector, the reapportionment of the pixel intensities in accordance with the invention allows the combination of the images taken at each position to nonetheless present a consistent and accurate diffraction image, as would be collected by a cylindrical detector.

In one embodiment of the invention, determining the spatial overlap of the pixels of the projected pixel array and the virtual detection surface and reapportioning the X-ray intensities includes breaking each pixel space into subpixels, and redistributing the subpixels among adjacent pixels according to the overlap. The quantitative redistribution of subpixels thereby facilitates the proper reapportionment of pixel intensities. In an exemplary embodiment, the subpixels for a given pixel each represent an equal portion of the total X-ray intensity for that pixel.

In a system applying the method of the invention, a detector output module may receive the pixel outputs at each of the plurality of radial directions and perform the reapportionment of the pixel intensities. The output module may be part of a control system for controlling the operation of the goniometer and the detector, and may be part of a host computer for the system.

BRIEF DESCRIPTION OF THE DRAWINGS

FIG. 7 is a schematic illustration of the smearing effect produced by superimposing sequential frames using a two-dimensional X-ray detector.

FIG. 8A is a schematic illustration of the pixel layout on a two-dimensional X-ray detector.

FIG. 8B is a schematic illustration of the pixel layout of a two-dimensional pixel layout when projected onto a cylindrical surface.

DETAILED DESCRIPTION

Figure 1A:
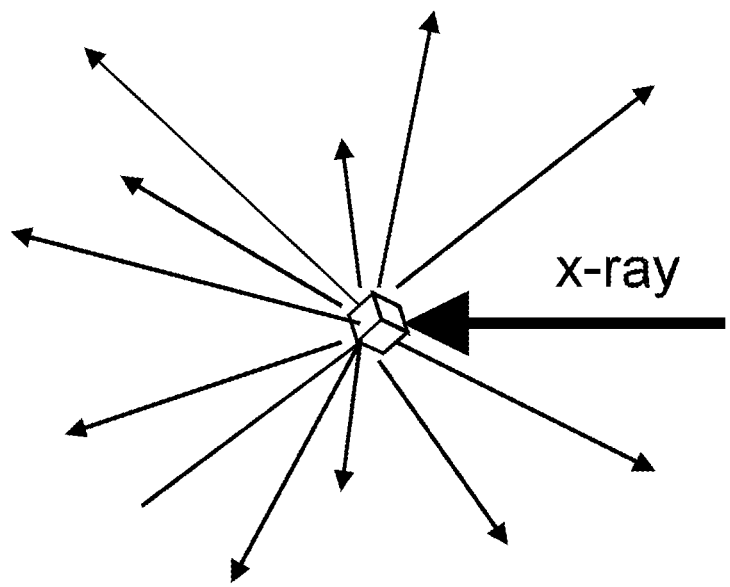
FIG. 1A is a schematic representation of X-rays diffracted from a single crystal sample.
Figure 1B:
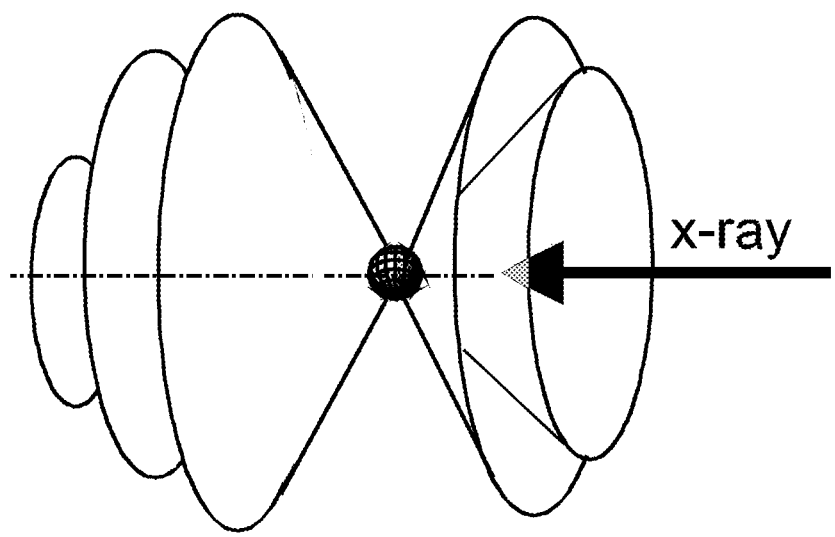
FIG. 1B is a schematic representation of X-rays diffracted from a polycrystalline sample.
Figure 2:
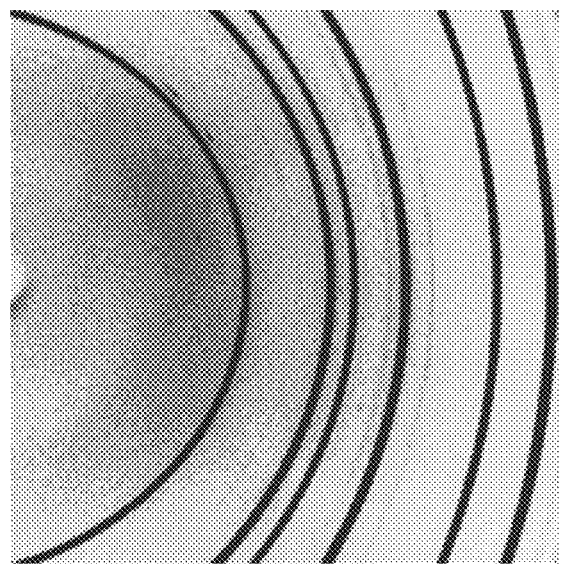
FIG. 2 is an image of a two-dimensional diffraction pattern of corundum showing the corresponding diffraction rings.
Figure 3:
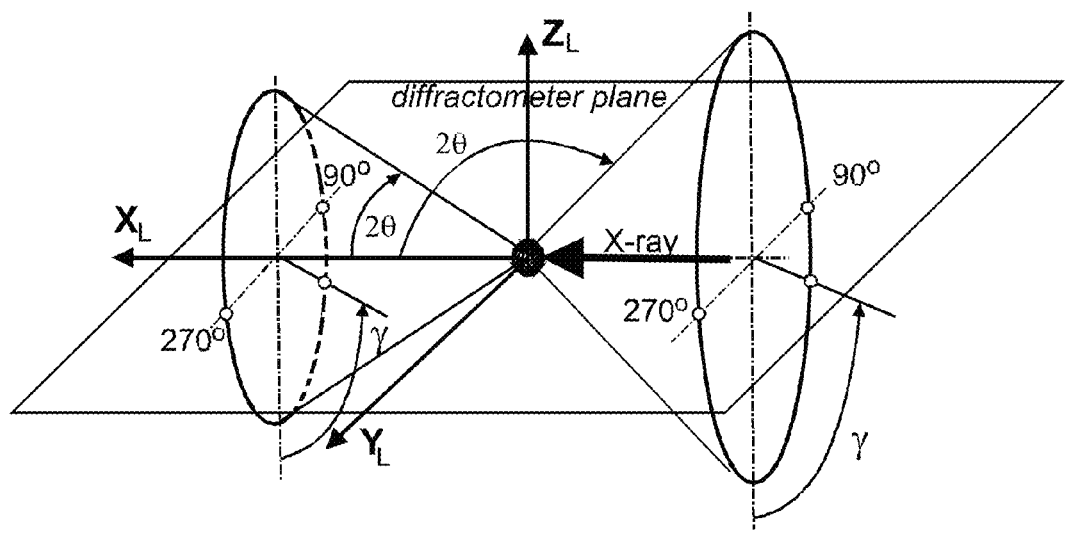
FIG. 3 is a schematic representation of the geometric relationship of diffraction rings in a diffractometer.
Figure 4:
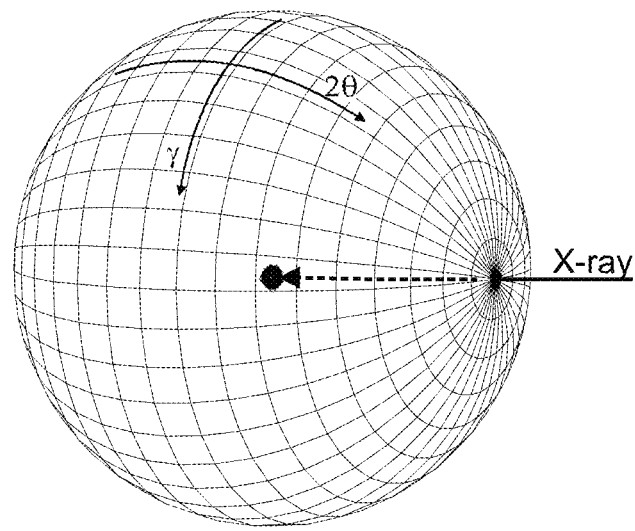
FIG. 4 is a schematic representation of an ideal spherical X-ray diffraction detector.
Figure 5:
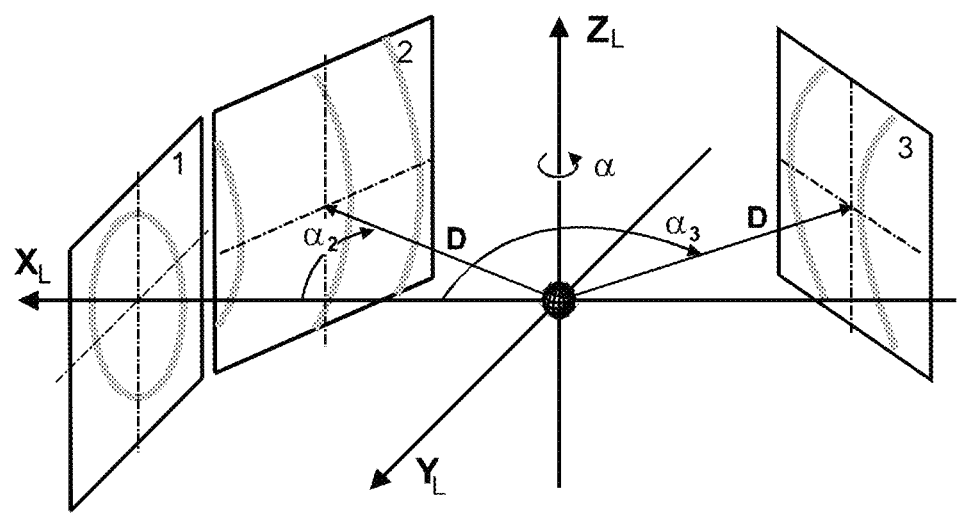
FIG. 5 is a schematic illustration showing diffraction rings detected by a two-dimensional detector at different detector positions in accordance with the present invention.

Shown in FIG. 5 is a schematic view of a flat, 2D detector at different positions during an X-ray diffraction scan. In this example, the system is shown using laboratory coordinates $X_L Y_L Z_L$. The detection surface can be viewed as a plane which, at each position, intersects the diffraction cone to form a conic section. The detector position is defined by the sample-to-detector distance D and the detector swing angle $\alpha$. D is the perpendicular distance from the goniometer center to the detection plane and $\alpha$ is a right-handed rotation angle about the $Z_L$ axis. At position 1, the center of the detector is located on the positive side of $X_L$ axis, such that $\alpha=0$. Each of detector positions 2 and 3 are rotated away from $X_L$ axis with negative swing angles (i.e., $\alpha<0$), identified, respectively, as $\alpha_2$ and $\alpha_3$. Because of the two-dimensional area of the detector, at a given detector angle $\alpha$, a range of $2\theta$ values can be measured.

As can be seen from FIG. 5, a diffraction frame collected by a 2D detector at a particular position includes a limited angular range. One way to extend the angular range is by merging multiple frames collected at different swing angles. Another method is to scan over a large $2\theta$ range by rotating the 2D detector about the $Z_L$ axis. As shown schematically in FIG. 6, a 2D detector may be mounted in an orientation that is perpendicular to the diffractometer plane and perpendicular to a line in the diffractometer plane that defines the minimum distance to the detector surface. The length of this line also represents the distance D between the detection plane and the instrument center and, together with the swing angle $\alpha$, can be used to define the detector position, as described above. The detector swing angle $\alpha$ is defined as the angle measured between the $X_L$ axis and the line between the instrument center and the detection surface.

The intersection (o) of the line and detector may be referred to as the detector center, and represents the origin of a two-dimensional x-y coordinate system within the plane of the detector. Thus, the location of any pixel in the 2D detector may be defined by its pixel position (x, y) within this coordinate system. During the data collection scan, the swing angle $\alpha$ changes continuously or in steps while collecting the X-ray counts with the detector. Therefore, during the scan of the detector about the $Z_L$ axis, the y-axis of the detector traces a cylindrical surface during the data collection, as shown in FIG. 6.

Figure 6:
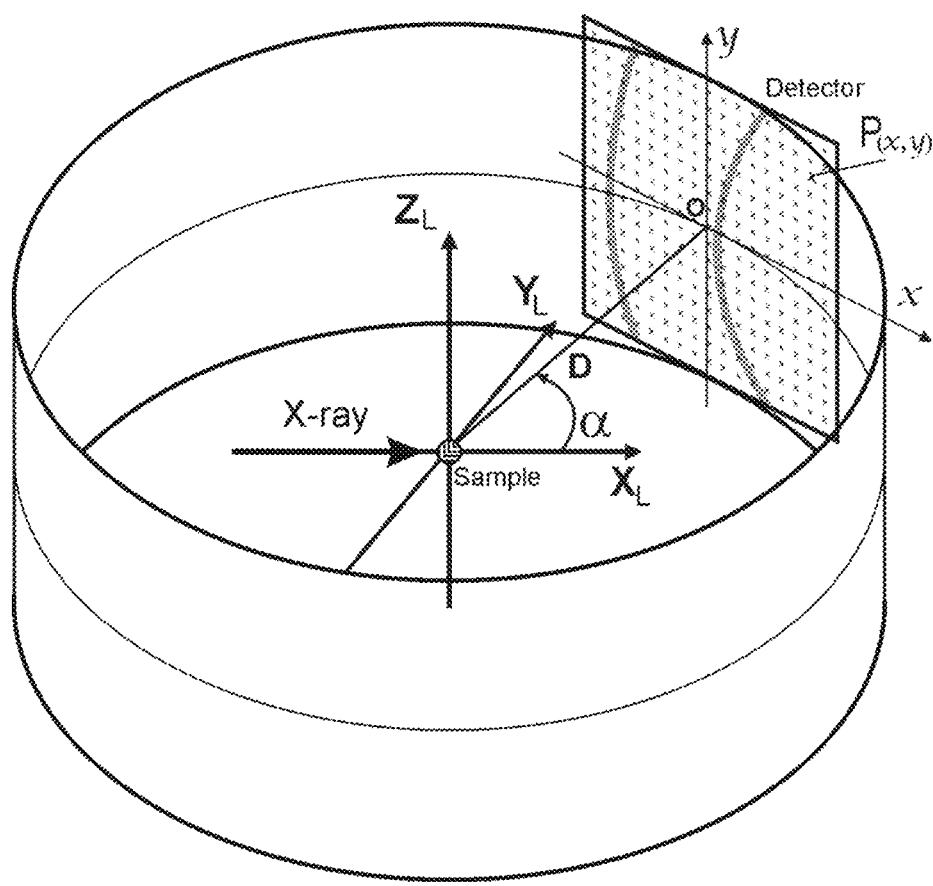
FIG. 6 is a schematic illustration of a two-dimensional detector according to the present invention relative to a detection circle around a sample.

Using the parameters shown in FIG. 6, the distance of a particular point (or pixel) on the detector, P(x,y), to the sample may be described as:

$$R(x,y)=\sqrt{D^2+x^2+y^2} \quad (1)$$

If the size of a particular pixel is given as $\Delta x$ and $\Delta y$ (i.e., the width, $\Delta x$, of the pixel in the detector x-direction, and the height, $\Delta y$, of the pixel in the detector y-direction, the solid angle covered by a pixel centered at P(x,y) may be represented as:

$$\Delta\Omega = \frac{\Delta x \cdot \Delta y \cdot D}{R^3(x, y)} \quad (2)$$

The $2\theta$ and $\gamma$ values of the point P(x,y) on the flat 2D detector are given as:

$$2\theta = \arccos\frac{x\sin\alpha + D\cos\alpha}{\sqrt{D^2+x^2+y^2}}, (0<2\theta<\pi) \quad (3)$$

$$\gamma = \frac{x\cos\alpha - D\sin\alpha}{|x\cos\alpha - D\sin\alpha|}\arccos\frac{-y}{\sqrt{y^2+(x\cos\alpha - D\sin\alpha)^2}}, \quad (4)$$

$(-\pi < \gamma \leq \pi)$

During the data collection scan, X-ray diffraction data is collected at each of the pixels of the 2D detector. However, as can be seen from FIG. 6, there is a variable pixel-to-sample distance for the different pixels depending on their location on the detection surface relative to the detection center o. The further a pixel is from the center, the larger the pixel-to-sample distance. As the detector is moved along the scan direction, a given diffracted X-ray beam will be detected by different pixels of the detector, which is moving relative to the beam. FIG. 7 shows a series of detector frames distributed across the scanning range of the detector, with a corresponding image of the detected diffraction rings shown underneath. Since there will be slight differences in the frames with regard to the relative position of the X-ray energy detected away from the detector center (the differences increasing toward the detector edges), merely combining this information results in a smearing of the recorded position of the diffraction rings, as shown in the lower portion of FIG. 7.

In order to provide more accurate position data for a system like that described above, the present invention projects all the frames detected by the 2D detector onto a cylindrical surface based on the scattering angle from the incident beam. This scattering angle can be given by the 2θ and γ angles or a different set of angles. Typically, the pixels of a flat 2D detector each cover a square (or rectangular) area, and all have the same shape and size, as illustrated in the schematic diagram of FIG. 8A. However, when projecting these pixels onto a cylindrical surface, the relative shape of the pixels is dependent on their respective distance from the detector origin o, as shown in FIG. 8B. The projected image therefore gives the correct scattering angles for all projected pixels and all of the projected images collected at sequential detector positions are adapted to the same cylindrical surface. As such, the scanned image by superposition of the cylindrical projections will accurately show the diffraction rings without a smearing effect. Those skilled in the art will understand that, while this embodiment uses a similar number of pixels for the virtual cylindrical detection surface as exists in the two-dimensional detector, it is not necessary to maintain a one-to-one correspondence between the pixels of each.

Figure 9:
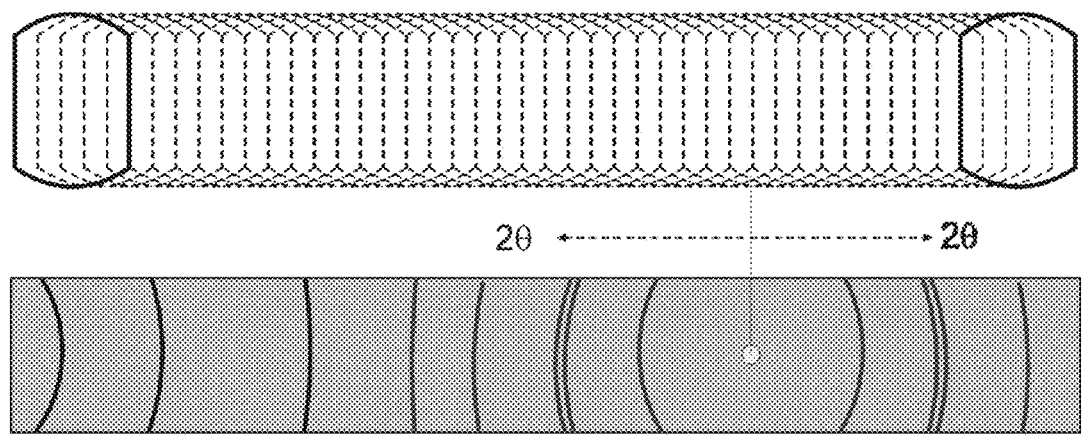
FIG. 9 is a schematic illustration of the absence of smearing when the cylindrical projections from sequential two-dimensional frames are combined.

FIG. 9 is a schematic illustration similar to that of FIG. 7, but in which the indicated detector frames have been projected onto a cylindrical surface. Because of this projection, the relative diffraction data from frame-to-frame is properly aligned, and summing the frames provides a mapping of the diffraction rings that is clear and without smearing, as shown in the lower portion of FIG. 9. However, proper projection of the flat, 2D detector surface onto a cylindrical surface requires that the data detected by the respective pixels of the detector be properly assigned to the corresponding virtual pixels of the cylindrical surface.

Figure 10:
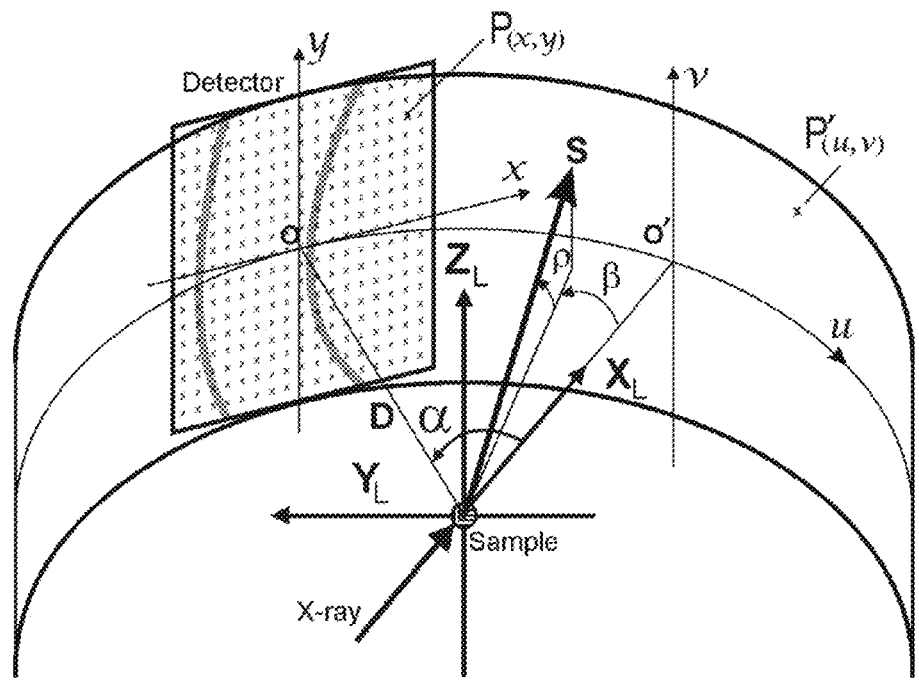
FIG. 10 is a schematic representation of the projection of a two-dimensional detector image onto a cylindrical surface.

A geometrical relationship between the flat 2D image and the cylindrical virtual surface in laboratory coordinates is depicted in FIG. 10. The intersection between the $X_L$ axis and the cylindrical surface may be used as the origin, o' of the cylindrical surface. The image on the cylindrical surface will be displayed as a flat image with axes u and v in rectangular coordinates. The direction of an arbitrary scattered beam S can be given by the diffraction parameters 2θ and γ. Any point on the flat detector can be projected onto the cylindrical surface by following a particular direction given by the 2θ and γ values. The 2θ and γ values for a point on the flat detector can, in turn, be calculated from its detector coordinates x and y. The u and v values on the cylindrical surface can then be calculated from 2θ and γ based on equations known in the art (see, for example, Bob He, "*Two-dimensional X-ray Diffraction*", John Wiley & Sons, (2009)). An alternative geometry given by the angle β and ρ may also be used, and can often simplify the calculation. In such a geometry, β is the angle between an arbitrary scattered beam, S, and $X_L$, as projected on the diffractometer plane $X_L$-$Y_L$. The rotation axis of β is the $Z_L$ axis, which is also the axis of the cylindrical surface. The value ρ represents the angle between S and the diffractometer plane.

For the flat 2D detector, the scattering angle of a point P(x,y), in terms of β and ρ, can be given as:

$$\rho = \arctan\frac{y}{\sqrt{x^2 + D^2}} \quad (5)$$

and $$\beta = \alpha - \arctan\frac{x}{D} \quad (6)$$

For the cylindrical image, the scattering angle of a point P'(u,v) is given as:

$$\rho' = \arctan\frac{v}{D} \quad (7)$$

and $$\beta' = -\frac{u}{D} \quad (8)$$

Any point on the flat 2D detector should be projected to the point on the cylindrical surface with the same scattering angle, i.e., ρ=ρ' and β=β'. Therefore, we can derive the following projection equations from the above four equations:

$$u = D\left(\arctan\frac{x}{D} - \alpha\right) \quad (9)$$

$$v = \frac{Dy}{\sqrt{x^2 + D^2}} \quad (10)$$

Figure 11:
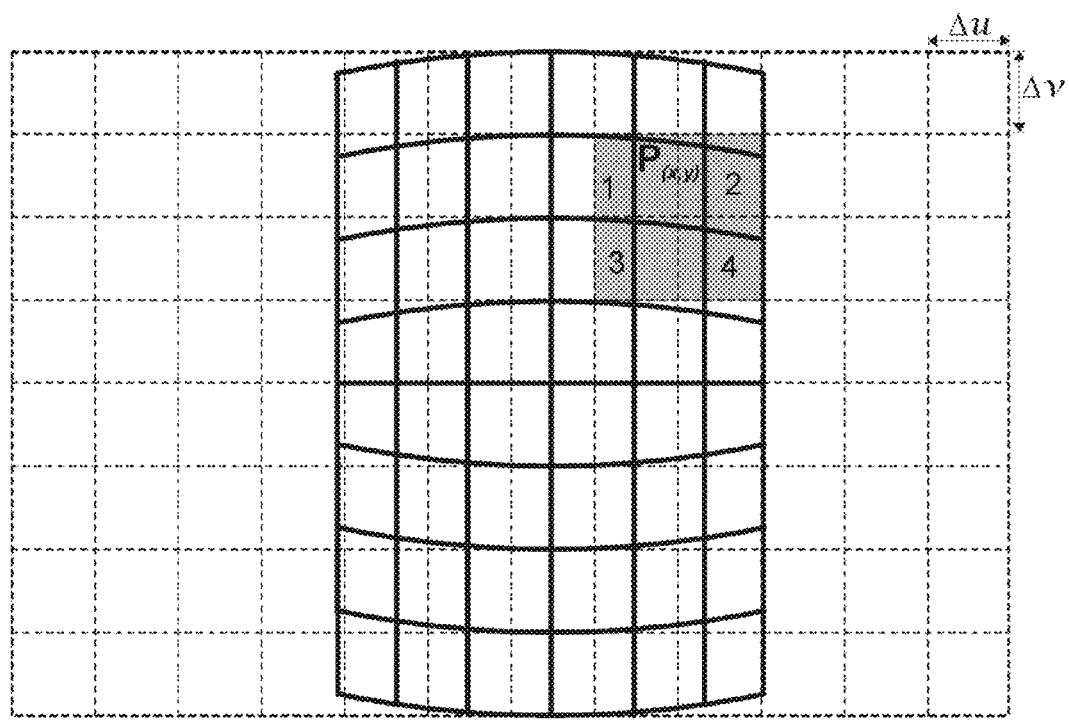
FIG. 11 is a schematic illustration of the pixel overlap between a projected two-dimensional detector image and a cylindrical pixel space.

FIG. 11 shows the pixel-to-pixel correspondence when projecting a pixel of the flat 2D detector onto the flattened image of the cylindrical surface. Each pixel in the flat 2D detector projected to the cylindrical image defined by the box of solid lines. The pixels of the cylindrical image are defined by the grid of dotted lines, each having a pixel size of Δu×Δv. Due to the projection geometry described above, each pixel from the flat 2D detector may contribute to several pixels in the cylindrical image. For example, the pixel $P_{(x,y)}$ shown in the flat 2D detector of FIG. 11 overlaps to some extent with four different pixels in the cylindrical image. As such, X-ray energy detected by $P_{(x,y)}$ should be distributed to each of the four virtual pixels of the cylindrical surface. Thus, a degree of overlap between the pixels of the detector and those of the cylindrical surface must be accounted for to get an accurate projection.

Figure 12:
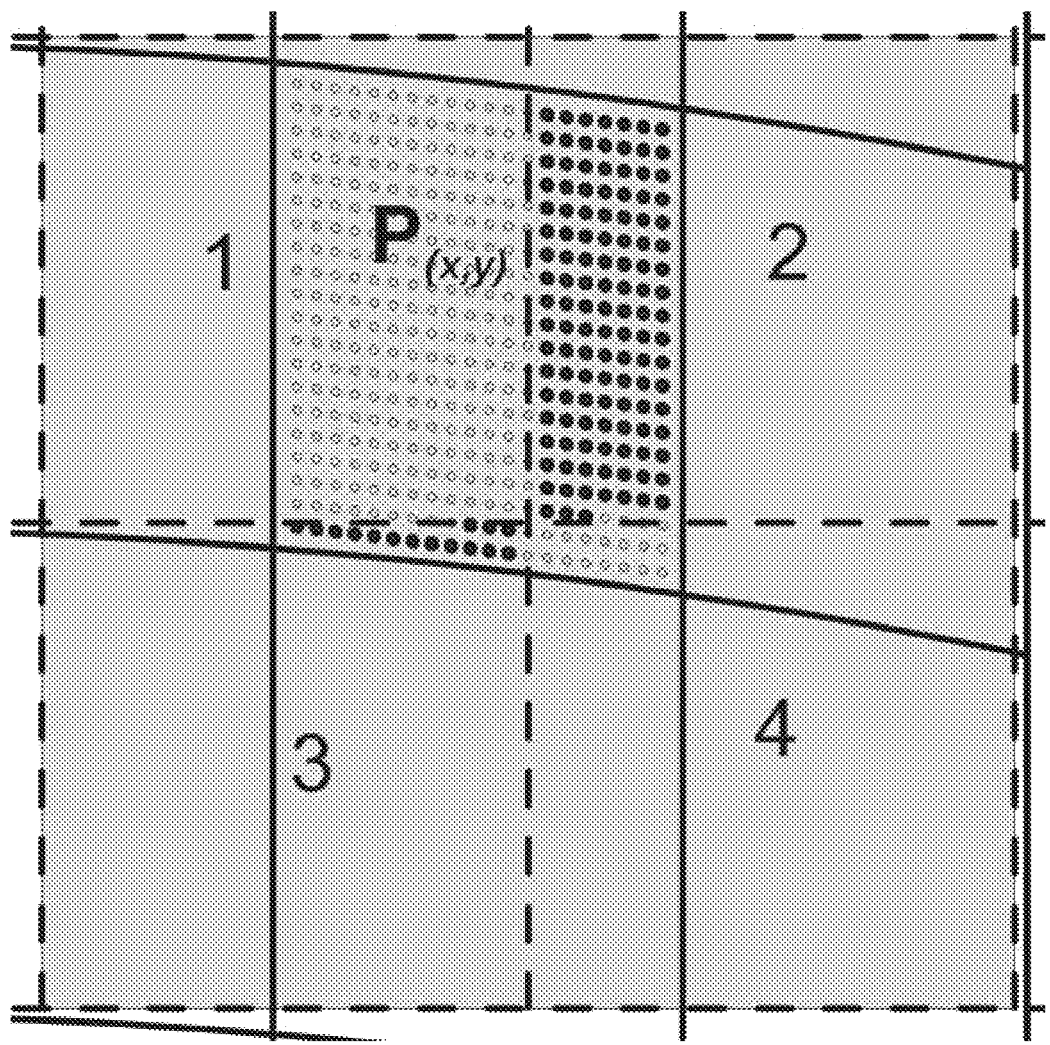
FIG. 12 is a schematic illustration of the use of subpixels in reapportioning intensity values detected by detector pixels.

Different methods may be used to get an accurate projection of the pixels. For example, The areas of the pixel $P_{(x,y)}$ that overlap, respectively, with pixels 1, 2, 3 and 4 shown in FIG. 11 may be calculated using equations (9) and (10) above. The intensity counts collected by the pixel $P_{(x,y)}$ can then be distributed to the pixels 1, 2, 3 and 4 in a proportional manner relative to the respective area of overlap for each. However, the area of the pixel is difficult to calculate due to the curved pixel boundaries. An alternative approach is to divide the intensity count of each pixel in the flat 2D image among a set of identical subpixels equally distributed within the pixel space, as shown in FIG. 12. In this representation, the subpixels are discrete points evenly distributed inside the pixel area and are marked by circles or dark spots.

In the subpixel distribution of FIG. 12, if the total number of subpixels within each pixel is M, the scattering intensity count assigned to each subpixel is the total count divided by M. Thus, the subpixels falling into cylindrical pixel 1 (shown as circles in the upper-left region of the pixel space of $P_{(x, y)}$) are assigned to that pixel. Similarly, the subpixels falling, respectively, into the one of the regions of pixels 2, 3 and 4 are assigned to that subpixel. Since each subpixel in the flat 2D image can be located in the cylindrical image by equation (9) and (10), this allows for assignment of the subpixels, and their corresponding intensity values, to the appropriate pixels of the cylindrical surface. In this way, the smearing effect is eliminated and an accurate localization of the diffraction rings may be determined.

The diffraction space coordinates (2θ, γ) for a pixel or any point P(u,v) in the cylindrical image can be calculated from the following two equations:

$$2\theta = \arccos\left[D\cos\left(\frac{u}{D}\right)\bigg/ \sqrt{D^2 + v^2}\,\right], \; (0 < 2\theta < \pi) \quad (11)$$

$$\gamma = \frac{u}{|u|}\arccos\left[-v \bigg/ \sqrt{v^2 + D^2\sin^2\left(\frac{u}{D}\right)}\,\right] \; (-\pi < \gamma \le \pi) \quad (12)$$

These equations may be used to integrate the diffraction data into a 2θ or γ-profile. Once the diffraction space coordinates (2θ, γ) of each pixel in the cylindrical image are determined, most data analysis approaches developed for the flat detectors are applicable.

Figure 13:
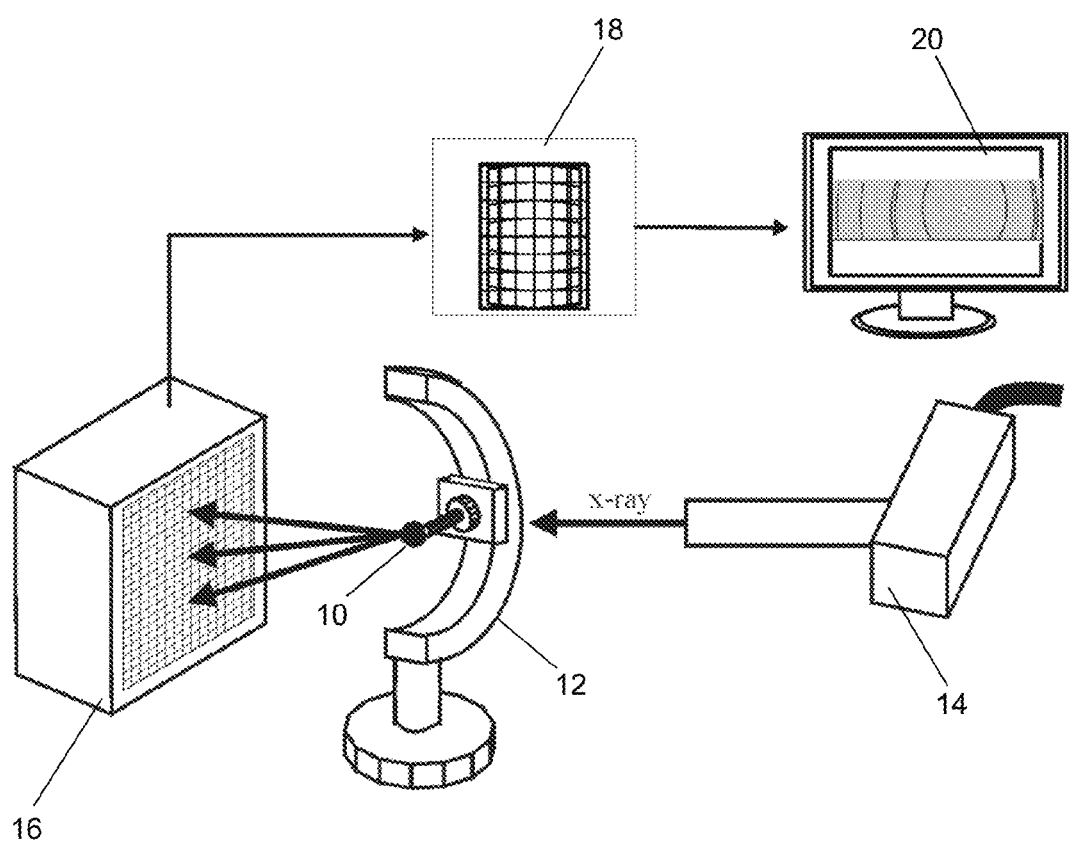
FIG. 13 is a schematic illustration of a system according to the present invention.

Shown in FIG. 13 is a system according to the invention including the sample 10, goniometer 12, X-ray beam source 14 and X-ray detector 16. Also shown is detector output module 18, which receives the outputs from each of the detector pixels, and performs the reapportionment of the pixel intensities as described above. In an exemplary embodiment of the invention, the output module 18 is part of a host computer 20 used for controlling the system components and conducting the diffraction scan accordingly. However, the output module 18 may also be part of the detector unit itself, or it may be a separate unit altogether. Those skilled in the art will recognize that different configurations in this regard are possible.

While the invention has been shown and described with reference to specific embodiments thereof, it will be recognized that various changes in form and detail may be made herein without departing from the spirit and scope of the invention as defined by the appended claims.

The invention claimed is:

1. A method of performing an X-ray diffraction analysis of a sample comprising:
   a) locating the sample in a goniometer, the location of the sample representing an origin of a three-dimensional coordinate system having mutually perpendicular $X_L$, $Y_L$ and $Z_L$ axes;
   b) illuminating the sample with an X-ray beam directed along the $X_L$-axis such that diffracted X-rays are emitted from the sample along a range of diffraction angles;
   c) detecting diffracted X-rays with a two-dimensional X-ray detector having a minimum distance D from a center of the sample along a radial direction in the $X_L$-$Y_L$ plane that is substantially perpendicular to a surface of the detector, the detector surface being substantially planar and comprising an array of detector pixels located in a two-dimensional pixel array space;
   d) projecting the two-dimensional pixel array space along said range of diffraction angles onto a cylinder having a radius relative to the $Z_L$ axis of length equal to said distance D to form a projected pixel array space;
   e) determining a virtual cylindrical detection surface on said cylinder, said detection surface having an array of virtual pixels;
   f) determining a spatial overlap between pixels of the projected pixel array space and the virtual pixels of the virtual detection surface, and reapportioning X-ray intensities attributable to each pixel of the detector based on said spatial overlap such that the reapportioned pixel intensities represent those which would have been detected by a cylindrical detector having a detection surface at said virtual cylindrical detection surface;
   g) moving the detector in a circular path around the sample while maintaining said minimum distance D and repeating steps (c) through (f) at a plurality of radial directions in the $X_L$-$Y_L$ plane until a final radial position of the detector is reached; and
   h) combining the reapportioned pixel intensities collected at each radial position relative to diffraction angle.

2. A method according to claim 1 wherein moving the detector comprises moving the detector in a step-wise manner.

3. A method according to claim 1 wherein moving the detector comprises moving the detector in a continuous manner.

4. A method according to claim 1 wherein the pixels of the detector are all substantially equal in size.

5. A method according to claim 1 wherein there is a one-to-one correspondence between the pixels of the projected pixel array space and the virtual pixels of the virtual cylindrical detection surface.

6. A method according to claim 1 wherein diffracted X-rays emitted along the same diffraction angle are detected by the detector for at least two of said plurality of radial directions.

7. A method according to claim 1 wherein said reapportioning of X-ray intensities comprises dividing each pixel space into a finite number of subpixels, and redistributing the subpixels among adjacent pixels according to the degree of spatial overlap with each of said adjacent pixels.

8. A method according to claim 7, wherein the subpixels for a given pixel each represent an equal portion of the total X-ray intensity for that pixel.

9. A method of performing an X-ray diffraction analysis of a sample comprising:
   a) locating the sample in a goniometer, the location of the sample representing an origin of a three-dimensional coordinate system having mutually perpendicular $X_L$, $Y_L$ and $Z_L$ axes;
   b) illuminating the sample with an X-ray beam directed along the x-axis such that diffracted X-rays are emitted from the sample along a range of diffraction angles;
   c) detecting diffracted X-rays with a two-dimensional X-ray detector having a detection center a distance D from a center of the sample along a radial direction in the $X_L$-$Y_L$ plane that is substantially perpendicular to a surface of the detector, the detector surface being substantially planar and comprising an array of detector pixels located in a two-dimensional pixel array space;

d) projecting the two-dimensional pixel array space along said range of diffraction angles onto a cylinder having a radius relative to the $Z_L$ axis of length equal to said distance D to form a projected pixel array space;

e) determining a virtual cylindrical detection surface having a detection center substantially co-located with the detection center of the detector and its axis along the $Z_L$ axis, said virtual cylindrical detection surface having an array of virtual pixels of substantially equal area each of which corresponds to one of the detector pixels;

f) determining a spatial overlap between pixels of the projected pixel array space and the virtual pixels of the virtual detection surface, and reapportioning X-ray intensities attributable to each pixel of the detector based on said spatial overlap such that the reapportioned pixel intensities represent those which would have been detected by a cylindrical detector having a detection surface at said virtual cylindrical detection surface;

g) moving the detector in a circular path around the sample while maintaining said minimum distance D and repeating steps (c) through (f) at a plurality of radial directions in the $X_L$-$Y_L$ plane until a final radial position of the detector is reached; and h) combining the reapportioned pixel intensities collected at each radial position relative to diffraction angle.

10. An X-ray diffraction analysis system for performing an X-ray diffraction analysis of a sample comprising:

a goniometer in which the sample is located, the location of the sample representing an origin of a three-dimensional coordinate system having mutually perpendicular $X_L$, $Y_L$ and $Z_L$ axes;

an X-ray beam source that illuminates the sample with an X-ray beam directed along the x-axis such that diffracted X-rays are emitted from the sample along a range of diffraction angles;

a two-dimensional X-ray detector that has a minimum distance D from a center of the sample along a radial direction in the $X_L$-$Y_L$ plane substantially perpendicular to a surface of the detector, the detector surface being substantially planar and comprising an array of detector pixels located in a two-dimensional pixel array space each of which detects X-ray energy incident upon it and outputs a corresponding pixel intensity, the detector moving in a circular path around the sample while maintaining said minimum distance D and detecting the diffracted X-rays at a plurality of radial directions in the $X_L$-$Y_L$ plane; and a detector output module that receives said pixel outputs at each of said plurality of radial directions and reapportions the pixel intensities based on a projection of the two-dimensional pixel array space along said range of diffraction angles onto a cylinder having a radius relative to the $Z_L$ axis of length equal to said distance D to form a projected pixel array space, and a spatial overlap of the pixels of the projected pixel array space with virtual pixels of a virtual cylindrical detection surface on said cylinder, the output module combining the reapportioned pixel intensities from each radial direction such that said combined intensities represent X-ray intensities which would have been detected by a cylindrical detector having a detection surface at said virtual cylindrical detection surface.

11. A system according to claim 10 wherein the detector moves in a step-wise manner.

12. A system according to claim 10 wherein the detector moves in a continuous manner.

13. A system according to claim 10 wherein the pixels of the detector are all substantially equal in size.

14. A system according to claim 10 wherein there is a one-to-one correspondence between the pixels of the projected pixel array space and the virtual pixels of the virtual cylindrical detection surface.

15. A system according to claim 10 wherein diffracted X-rays emitted along the same diffraction angle are detected by the detector for at least two of said plurality of radial directions.

16. A system according to claim 10 wherein said reapportioning of X-ray intensities comprises dividing each pixel space into a finite number of subpixels, and redistributing the subpixels among adjacent pixels according to the degree of spatial overlap with each of said adjacent pixels.

17. A system according to claim 10 wherein the subpixels for a given pixel each represent an equal portion of the total X-ray intensity for that pixel.

18. A system according to claim 10 wherein the output module is part of a control system for controlling the operation of the goniometer and the detector.

19. A system according to claim 18 wherein the control system comprises a host computer.

\* \* \* \* \*